United States Patent
Pacetti (12)

(10) Patent No.: US 7,014,913 B2
(45) Date of Patent: *Mar. 21, 2006

(54) RATE-REDUCING MEMBRANE FOR RELEASE OF AN AGENT

(75) Inventor: Stephen D. Pacetti, San Jose, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/760,132

(22) Filed: Jan. 15, 2004

(65) Prior Publication Data

US 2004/0234737 A1    Nov. 25, 2004

Related U.S. Application Data

(63) Continuation of application No. 09/966,787, filed on Sep. 27, 2001, now Pat. No. 6,753,071.

(51) Int. Cl.
*B32B 7/02* (2006.01)
*B32B 27/06* (2006.01)
*B32B 27/08* (2006.01)
*A61M 25/00* (2006.01)
*A61F 2/06* (2006.01)

(52) U.S. Cl. .................. 428/212; 623/1.11; 623/1.13; 623/1.15; 623/1.42; 623/1.43; 623/1.44; 623/1.46; 623/1.49; 427/2.1; 427/2.24; 427/2.25; 427/2.3; 427/384; 427/402; 427/407.1

(58) Field of Classification Search ............... 428/212, 428/35.8, 36.9, 36.91, 421, 422, 500, 522, 428/521, 523, 423.1, 446, 447, 457; 623/1.11, 623/1.13, 1.15, 1.42, 1.43, 1.44, 1.46, 1.49; 427/2.1, 2.24, 2.25, 2.3, 384, 402, 407.1
See application file for complete search history.

(56) References Cited

U.S. PATENT DOCUMENTS

| | | | |
|---|---|---|---|
| 3,828,777 A * | 8/1974 | Ness ........................ 424/427 |
| 4,329,383 A | 5/1982 | Joh |
| 4,459,252 A * | 7/1984 | MacGregor ............... 264/46.9 |
| 4,733,665 A | 3/1988 | Palmaz ...................... 128/343 |
| 4,800,882 A | 1/1989 | Gianturco .................. 128/343 |
| 4,882,168 A | 11/1989 | Casey et al. |
| 4,886,062 A | 12/1989 | Wiktor ....................... 128/343 |
| 4,931,287 A | 6/1990 | Bae et al. |
| 4,941,870 A | 7/1990 | Okada et al. |
| 4,977,901 A | 12/1990 | Ofstead ...................... 128/772 |
| 5,019,096 A | 5/1991 | Fox, Jr. et al. |

(Continued)

FOREIGN PATENT DOCUMENTS

EP      0 301 856        2/1989

(Continued)

OTHER PUBLICATIONS

Barath et al., *Low Dose of Antitumor Agents Prevents Smooth Muscle Cell Proliferation After Endothelial Injury*; JACC 13(2):252A (Abstract) (Feb. 1989).

(Continued)

*Primary Examiner*—Vivian Chen
(74) *Attorney, Agent, or Firm*—Squire, Sanders & Dempsey L.L.P.

(57) ABSTRACT

A membrane that reduces the rate at which a therapeutic substance is released from an implantable medical device, such as a stent, is disclosed.

65 Claims, 1 Drawing Sheet

U.S. PATENT DOCUMENTS

| Patent No. | Date | Inventor(s) | Ref. |
|---|---|---|---|
| 5,059,211 A | 10/1991 | Stack et al. | 606/198 |
| 5,064,435 A | 11/1991 | Porter | |
| 5,071,407 A | 12/1991 | Termin et al. | |
| 5,078,736 A | 1/1992 | Behl | |
| 5,092,841 A | 3/1992 | Spears | |
| 5,112,457 A | 5/1992 | Marchant | 204/165 |
| 5,163,952 A | 11/1992 | Froix | 623/1 |
| 5,165,919 A | 11/1992 | Sasaki et al. | |
| 5,258,020 A | 11/1993 | Froix | |
| 5,272,012 A | 12/1993 | Opolski | |
| 5,292,516 A | 3/1994 | Viegas et al. | |
| 5,298,260 A | 3/1994 | Viegas et al. | |
| 5,300,295 A | 4/1994 | Viegas et al. | |
| 5,306,286 A | 4/1994 | Stack et al. | 606/198 |
| 5,306,501 A | 4/1994 | Viegas et al. | |
| 5,328,471 A | 7/1994 | Slepian | 604/101 |
| 5,330,768 A | 7/1994 | Park et al. | |
| 5,344,411 A | 9/1994 | Domb et al. | |
| 5,344,425 A | 9/1994 | Sawyer | |
| 5,380,299 A | 1/1995 | Fearnot et al. | |
| 5,417,981 A | 5/1995 | Endo et al. | |
| 5,447,724 A | 9/1995 | Helmus et al. | |
| 5,455,040 A | 10/1995 | Marchant | 424/426 |
| 5,462,990 A | 10/1995 | Hubbell et al. | |
| 5,464,650 A | 11/1995 | Berg et al. | 427/2.3 |
| 5,474,089 A | 12/1995 | Waynant | |
| 5,527,337 A | 6/1996 | Stack et al. | 606/198 |
| 5,569,463 A | 10/1996 | Helmus et al. | |
| 5,571,086 A | 11/1996 | Kaplan et al. | |
| 5,576,072 A | 11/1996 | Hostettler et al. | |
| 5,578,073 A | 11/1996 | Haimovich et al. | 623/1 |
| 5,605,696 A | 2/1997 | Eury et al. | 424/423 |
| 5,607,467 A | 3/1997 | Froix | |
| 5,609,629 A | 3/1997 | Fearnot et al. | |
| 5,616,338 A | 4/1997 | Fox, Jr. et al. | |
| 5,624,411 A | 4/1997 | Tuch | |
| 5,628,730 A | 5/1997 | Shapland et al. | 604/21 |
| 5,633,000 A | 5/1997 | Grossman et al. | 424/422 |
| 5,649,977 A | 7/1997 | Campbell | |
| 5,658,995 A | 8/1997 | Kohn et al. | |
| 5,662,960 A | 9/1997 | Hostettler et al. | |
| 5,667,767 A | 9/1997 | Greff et al. | 424/9.411 |
| 5,670,558 A | 9/1997 | Onishi et al. | 523/112 |
| 5,674,242 A | 10/1997 | Phan et al. | |
| 5,676,685 A | 10/1997 | Razavi | |
| 5,679,400 A | 10/1997 | Tuch | |
| 5,700,286 A | 12/1997 | Tartaglia et al. | 623/1 |
| 5,702,754 A | 12/1997 | Zhong | |
| 5,713,949 A | 2/1998 | Jayaraman | 623/1 |
| 5,716,981 A | 2/1998 | Hunter et al. | 514/449 |
| 5,723,219 A | 3/1998 | Kolluri et al. | |
| 5,728,152 A | 3/1998 | Mirsch, II et al. | |
| 5,735,897 A | 4/1998 | Buirge | |
| 5,746,998 A | 5/1998 | Torchilin et al. | |
| 5,762,638 A | 6/1998 | Shikani et al. | |
| 5,766,710 A | 6/1998 | Turnlund et al. | 428/36.1 |
| 5,769,883 A | 6/1998 | Buscemi et al. | 623/1 |
| 5,776,184 A | 7/1998 | Tuch | |
| 5,788,979 A | 8/1998 | Alt et al. | |
| 5,792,550 A | 8/1998 | Phillips et al. | |
| 5,800,392 A | 9/1998 | Racchini | 604/96 |
| 5,820,917 A | 10/1998 | Tuch | |
| 5,824,048 A | 10/1998 | Tuch | |
| 5,824,049 A | 10/1998 | Ragheb et al. | 623/1 |
| 5,830,178 A | 11/1998 | Jones et al. | 604/49 |
| 5,830,430 A | 11/1998 | Unger et al. | |
| 5,837,008 A | 11/1998 | Berg et al. | |
| 5,837,313 A | 11/1998 | Ding et al. | 427/2.21 |
| 5,843,156 A | 12/1998 | Slepian et al. | |
| 5,843,172 A | 12/1998 | Yan | 623/1 |
| 5,849,035 A | 12/1998 | Pathak et al. | |
| 5,849,368 A | 12/1998 | Hostettler et al. | |
| 5,851,508 A | 12/1998 | Greff et al. | 424/9.411 |
| 5,854,382 A | 12/1998 | Loomis | |
| 5,855,563 A | 1/1999 | Kaplan et al. | |
| 5,855,599 A | 1/1999 | Wan | |
| 5,858,746 A | 1/1999 | Hubbell et al. | 435/177 |
| 5,858,990 A | 1/1999 | Walsh | |
| 5,865,814 A | 2/1999 | Tuch | 604/265 |
| 5,869,127 A | 2/1999 | Zhong | |
| 5,873,904 A | 2/1999 | Ragheb et al. | 623/1 |
| 5,876,433 A | 3/1999 | Lunn | |
| 5,877,224 A | 3/1999 | Brocchini et al. | |
| 5,879,713 A | 3/1999 | Roth et al. | |
| 5,895,420 A | 4/1999 | Mirsch, II et al. | |
| 5,898,066 A | 4/1999 | Benowitz et al. | |
| 5,899,935 A | 5/1999 | Ding | |
| 5,911,702 A | 6/1999 | Romley et al. | |
| 5,919,570 A | 7/1999 | Hostettler et al. | |
| 5,925,720 A | 7/1999 | Kataoka et al. | |
| 5,932,299 A | 8/1999 | Katoot | |
| 5,945,115 A | 8/1999 | Dunn et al. | 424/422 |
| 5,951,458 A | 9/1999 | Hastings et al. | |
| 5,955,509 A | 9/1999 | Webber et al. | |
| 5,961,547 A | 10/1999 | Razavi | |
| 5,962,138 A | 10/1999 | Kolluri et al. | |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 5,997,517 A | 12/1999 | Whitbourne | |
| 6,005,020 A | 12/1999 | Loomis | |
| 6,010,530 A | 1/2000 | Goicoechea | 623/1 |
| 6,013,780 A | 1/2000 | Neufeld et al. | |
| 6,015,541 A | 1/2000 | Greff et al. | 424/1.25 |
| 6,017,577 A | 1/2000 | Hostettler et al. | |
| 6,022,901 A | 2/2000 | Goodman | |
| 6,026,316 A | 2/2000 | Kucharczyk et al. | |
| 6,028,164 A | 2/2000 | Loomis | |
| 6,030,656 A | 2/2000 | Hostettler et al. | |
| 6,033,582 A | 3/2000 | Lee et al. | |
| 6,040,058 A | 3/2000 | Hostettler et al. | |
| 6,042,875 A | 3/2000 | Ding et al. | 427/2.24 |
| 6,051,576 A | 4/2000 | Ashton et al. | |
| 6,051,648 A | 4/2000 | Rhee et al. | 525/54.1 |
| 6,056,938 A | 5/2000 | Unger et al. | |
| 6,056,993 A | 5/2000 | Leidner et al. | 427/2.25 |
| 6,060,451 A | 5/2000 | DiMaio et al. | 514/13 |
| 6,060,518 A | 5/2000 | Kabanov et al. | |
| 6,061,587 A | 5/2000 | Kucharczyk et al. | |
| 6,080,488 A | 6/2000 | Hostettler et al. | 428/423.3 |
| 6,086,773 A | 7/2000 | Dufresne et al. | |
| 6,096,070 A | 8/2000 | Ragheb et al. | 623/1 |
| 6,096,726 A | 8/2000 | Opolski | |
| 6,099,562 A | 8/2000 | Ding et al. | 623/1.46 |
| 6,102,046 A | 8/2000 | Weinstein et al. | |
| 6,110,188 A | 8/2000 | Narciso, Jr. | 606/153 |
| 6,110,483 A | 8/2000 | Whitbourne et al. | |
| 6,113,629 A | 9/2000 | Ken | 623/1.1 |
| 6,120,536 A | 9/2000 | Ding et al. | 623/1.43 |
| 6,120,847 A | 9/2000 | Yang et al. | 427/335 |
| 6,120,904 A | 9/2000 | Hostettler et al. | 428/423.3 |
| 6,121,027 A | 9/2000 | Clapper et al. | 435/180 |
| 6,126,649 A | 10/2000 | VanTassel et al. | |
| 6,129,761 A | 10/2000 | Hubbell | 623/11 |
| 6,136,006 A | 10/2000 | Johnson et al. | |
| 6,140,452 A | 10/2000 | Felt et al. | |
| 6,143,354 A | 11/2000 | Koulik et al. | |
| 6,153,252 A | 11/2000 | Hossainy et al. | 427/2.3 |
| 6,156,064 A | 12/2000 | Chouinard | |
| 6,156,350 A | 12/2000 | Constantz | |
| 6,159,232 A | 12/2000 | Nowakowski | |
| 6,159,978 A | 12/2000 | Myers et al. | |
| 6,162,244 A | 12/2000 | Braun et al. | |
| 6,165,212 A | 12/2000 | Dereume et al. | 623/1.13 |

| | | | | | | |
|---|---|---|---|---|---|---|
| 6,168,801 B1 | 1/2001 | Heil et al. ............... 424/426 | | 6,565,659 B1 | 5/2003 | Pacetti et al. |
| 6,177,523 B1 | 1/2001 | Reich et al. | | 6,572,644 B1 | 6/2003 | Moein |
| 6,178,346 B1 | 1/2001 | Amundson et al. | | 6,585,765 B1 | 7/2003 | Hossainy et al. |
| 6,179,817 B1 | 1/2001 | Zhong | | 6,585,926 B1 | 7/2003 | Mirzaee |
| 6,180,632 B1 | 1/2001 | Myers et al. | | 6,605,154 B1 | 8/2003 | Villareal |
| 6,183,469 B1 | 2/2001 | Thapliyal et al. | | 6,673,385 B1 | 1/2004 | Ding et al. |
| 6,197,051 B1 | 3/2001 | Zhong | | 6,753,071 B1 * | 6/2004 | Pacetti ................ 428/212 |
| 6,203,551 B1 | 3/2001 | Wu | | 6,790,228 B1 | 9/2004 | Hossainy et al. |
| 6,206,915 B1 | 3/2001 | Fagan et al. ............ 623/1.42 | | 2001/0007083 A1 | 7/2001 | Roorda |
| 6,211,247 B1 | 4/2001 | Goodman | | 2001/0014717 A1 | 8/2001 | Hossainy et al. ........... 525/60 |
| 6,214,901 B1 | 4/2001 | Chudzik et al. | | 2001/0018469 A1 | 8/2001 | Chen et al. ............. 523/121 |
| 6,231,600 B1 | 5/2001 | Zhong | | 2001/0020011 A1 | 9/2001 | Mathiowitz et al. |
| 6,238,364 B1 | 5/2001 | Becker | | 2001/0029351 A1 | 10/2001 | Falotico et al. |
| 6,240,616 B1 | 6/2001 | Yan | | 2001/0037145 A1 | 11/2001 | Guruwaiya et al. |
| 6,245,753 B1 | 6/2001 | Byun et al. | | 2001/0051608 A1 | 12/2001 | Mathiowitz et al. |
| 6,245,760 B1 | 6/2001 | He et al. | | 2002/0005206 A1 | 1/2002 | Falotico et al. |
| 6,248,129 B1 | 6/2001 | Froix | | 2002/0007213 A1 | 1/2002 | Falotico et al. |
| 6,249,952 B1 | 6/2001 | Ding | | 2002/0007214 A1 | 1/2002 | Falotico |
| 6,251,136 B1 | 6/2001 | Guruwaiya et al. | | 2002/0007215 A1 | 1/2002 | Falotico et al. |
| 6,254,632 B1 | 7/2001 | Wu et al. | | 2002/0009604 A1 | 1/2002 | Zamora et al. |
| 6,254,634 B1 | 7/2001 | Anderson et al. | | 2002/0016625 A1 | 2/2002 | Falotico et al. |
| 6,258,121 B1 | 7/2001 | Yang et al. ............ 623/1.46 | | 2002/0032414 A1 | 3/2002 | Ragheb et al. |
| 6,258,371 B1 | 7/2001 | Koulik et al. | | 2002/0032434 A1 | 3/2002 | Chudzik et al. |
| 6,261,320 B1 | 7/2001 | Tam et al. | | 2002/0051730 A1 | 5/2002 | Bodnar et al. |
| 6,262,034 B1 | 7/2001 | Mathiowitz et al. | | 2002/0077693 A1 | 6/2002 | Barclay et al. |
| 6,265,016 B1 | 7/2001 | Hostettler et al. | | 2002/0082679 A1 | 6/2002 | Sirhan et al. |
| 6,265,199 B1 | 7/2001 | Sheppard et al. | | 2002/0091433 A1 | 7/2002 | Ding et al. |
| 6,270,788 B1 | 8/2001 | Koulik et al. | | 2002/0111590 A1 | 8/2002 | Davila et al. |
| 6,274,164 B1 | 8/2001 | Novich | | 2002/0123801 A1 | 9/2002 | Pacetti et al. |
| 6,277,449 B1 | 8/2001 | Kolluri et al. | | 2002/0155212 A1 | 10/2002 | Hossainy |
| 6,283,947 B1 | 9/2001 | Mirzaee | | 2002/0165608 A1 | 11/2002 | Llanos et al. |
| 6,283,949 B1 | 9/2001 | Roorda | | 2002/0176849 A1 | 11/2002 | Slepian |
| 6,283,951 B1 | 9/2001 | Flaherty et al. | | 2002/0188037 A1 | 12/2002 | Chudzik et al. |
| 6,284,305 B1 | 9/2001 | Ding et al. | | 2003/0004141 A1 | 1/2003 | Brown |
| 6,287,249 B1 | 9/2001 | Tam et al. | | 2003/0028243 A1 | 2/2003 | Bates et al. |
| 6,287,628 B1 | 9/2001 | Hossainy et al. .......... 427/2.3 | | 2003/0028244 A1 | 2/2003 | Bates et al. |
| 6,290,729 B1 | 9/2001 | Slepian et al. | | 2003/0031780 A1 | 2/2003 | Chudzik et al. |
| 6,299,604 B1 | 10/2001 | Ragheb et al. | | 2003/0036794 A1 | 2/2003 | Ragheb et al. |
| 6,302,875 B1 | 10/2001 | Makower et al. | | 2003/0039689 A1 | 2/2003 | Chen et al. |
| 6,306,176 B1 | 10/2001 | Whitbourne | | 2003/0040790 A1 | 2/2003 | Furst |
| 6,306,177 B1 | 10/2001 | Felt et al. | | 2003/0060877 A1 | 3/2003 | Falotico et al. |
| 6,316,522 B1 | 11/2001 | Loomis et al. | | 2003/0065377 A1 | 4/2003 | Davila et al. |
| 6,322,771 B1 | 11/2001 | Linden et al. | | 2003/0073961 A1 | 4/2003 | Happ ..................... 604/274 |
| 6,331,313 B1 | 12/2001 | Wong et al. | | 2003/0083646 A1 | 5/2003 | Sirhan et al. |
| 6,334,867 B1 | 1/2002 | Anson | | 2003/0083739 A1 | 5/2003 | Cafferata |
| 6,335,029 B1 | 1/2002 | Kamath et al. | | 2003/0099712 A1 | 5/2003 | Jayaraman |
| 6,344,035 B1 | 2/2002 | Chudzik et al. | | 2004/0063805 A1 * | 4/2004 | Pacetti et al. ............ 523/113 |
| 6,346,110 B1 | 2/2002 | Wu | | 2004/0224001 A1 * | 11/2004 | Pacetti et al. ............ 424/423 |
| 6,358,556 B1 | 3/2002 | Ding et al. | | 2005/0106203 A1 | 5/2005 | Roorda et al. |
| 6,379,381 B1 | 4/2002 | Hossainy et al. ........ 623/1.42 | | | | |
| 6,387,379 B1 | 5/2002 | Goldberg et al. | | | FOREIGN PATENT DOCUMENTS | |
| 6,391,052 B1 | 5/2002 | Buirge | | | | |
| 6,395,326 B1 | 5/2002 | Castro et al. | | EP | 0 514 406 | 11/1992 |
| 6,410,044 B1 | 6/2002 | Chudzik | | EP | 0 604 022 | 6/1994 |
| 6,419,692 B1 | 7/2002 | Yang et al. | | EP | 0 623 354 | 11/1994 |
| 6,451,373 B1 | 9/2002 | Hossainy et al. | | EP | 0 627 226 | 12/1994 |
| 6,482,834 B1 | 11/2002 | Spada et al. | | EP | 0 665 023 | 8/1995 |
| 6,494,862 B1 | 12/2002 | Ray et al. | | EP | 0 701 802 | 3/1996 |
| 6,503,556 B1 | 1/2003 | Harish et al. ............ 427/2.24 | | EP | 0 716 836 | 6/1996 |
| 6,503,954 B1 | 1/2003 | Bhat et al. | | EP | 0 809 999 | 12/1997 |
| 6,506,437 B1 | 1/2003 | Harish et al. | | EP | 0 832 655 | 4/1998 |
| 6,524,347 B1 | 2/2003 | Myers et al. | | EP | 0875218 | 4/1998 |
| 6,527,801 B1 | 3/2003 | Dutta | | EP | 0 850 651 | 7/1998 |
| 6,527,863 B1 | 3/2003 | Pacetti et al. | | EP | 0 879 595 | 11/1998 |
| 6,528,526 B1 | 3/2003 | Myers et al. | | EP | 0 923 953 | 6/1999 |
| 6,530,950 B1 | 3/2003 | Alvarado et al. | | EP | 0 953 320 | 11/1999 |
| 6,530,951 B1 | 3/2003 | Bates et al. | | EP | 0 970 711 | 1/2000 |
| 6,540,776 B1 | 4/2003 | Sanders Millare et al. | | EP | 0 982 041 | 3/2000 |
| 6,544,223 B1 | 4/2003 | Kokish | | EP | 1 023 879 | 8/2000 |
| 6,544,543 B1 | 4/2003 | Mandrusov et al. | | EP | 1 273 314 | 1/2003 |
| 6,544,582 B1 | 4/2003 | Yoe | | JP | 11299901 | 11/1999 |
| 6,555,157 B1 | 4/2003 | Hossainy | | JP | 2001-190687 | 7/2001 |
| 6,558,733 B1 | 5/2003 | Hossainy et al. | | WO | WO 90/01969 | 3/1990 |

| | | |
|---|---|---|
| WO | WO 91/12846 | 9/1991 |
| WO | WO 95/10989 | 4/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/17331 | 4/1998 |
| WO | WO 98/23228 | 6/1998 |
| WO | WO 98/36784 | 8/1998 |
| WO | WO 99/01118 | 1/1999 |
| WO | WO 99/16386 | 4/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/74414 | 10/2001 |
| WO | WO 02/03890 | 1/2002 |
| WO | WO 02/026162 | 4/2002 |
| WO | WO 02/34311 | 5/2002 |
| WO | WO 02/056790 | 7/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |

OTHER PUBLICATIONS

Burrell, *Solubility Parameter Values*, Inmont Corp., pp. IV-337-359.

Dichek et al., *Seeding of Intravascular Stents with Genetically Engineered Endothelial Cells*, Circ. 80(5):1347-1353 (1989).

Matsumaru et al., *Embolic Materials For Endovascular Treatment of Cerebral Lesions*; J. Biomater. Sci. Polymer Edn, 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull., 33(6):2490-2498 (1985).

Miyazawa et al., *Effects of Pemirolast and Tranilast on Intimal Thickening After Arterial Injury in the Rat*; J. Cardiovasc. Pharmacol., pp. 157-162 (1997).

Ohsawa et al., *Preventive Effects of an Antiallergic Drug, Pemirolast Potassium, on Restenosis After Percutaneous Transluminal Coronary Angioplasty*; American Heart Journal; pp. 1081-1087 (1998).

Shigeno, *Prevention of Cerebrovascular Spasm By Bosentan, Novel Endothelin Receptor*, Chemical Abstract 125:212307 (1996).

U.S. Appl. No. 09/676,049, filed Sep. 28, 2000, Castro et al.
U.S. Appl. No. 09/894,293, filed Jun. 27, 2001, Roorda.
U.S. Appl. No. 10/176,510, filed Jun. 21, 2002, Hossainy et al.
U.S. Appl. No. 10/177,117, filed Jun. 21, 2002, Hossainy.
U.S. Appl. No. 10/177,154, filed Jun. 21, 2002, Hossainy et al.
U.S. Appl. No. 10/198,912, filed Jul. 19, 2002, Ding et al.
U.S. Appl. No. 10/320,899, filed Dec. 16, 2002, Shah et al.
U.S. Appl. No. 10/376,348, filed Feb. 26, 2003, Ding et al.
U.S. Appl. No. 10/428,691, filed May 1, 2003, Pacetti.

* cited by examiner

RATE-REDUCING MEMBRANE FOR RELEASE OF AN AGENT

CROSS REFERENCE

This is a continuation of application Ser. No. 09/966,787 filed on Sep. 27, 2001 now U.S. Pat. No. 6,753,071.

BACKGROUND OF THE INVENTION

1. Field of the Invention

The invention relates to a coating disposed on an implantable device, one example of which is a stent, for reducing the release rate of an agent carried by the device.

2. Description of the Background

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to remodel the vessel wall. The balloon is then deflated to a smaller profile to allow the catheter to be withdrawn from the patient's vasculature.

A problem associated with the above procedure includes formation of intimal flaps or torn arterial linings, which can collapse and occlude the conduit after the balloon is deflated. Vasospasms and recoil of the vessel wall also threaten vessel closure. Moreover, thrombosis and restenosis of the artery may develop over several months after the procedure, which may necessitate another angioplasty procedure or a surgical by-pass operation. To reduce the partial or total occlusion of the artery by the collapse of arterial lining and to reduce the chance of the development of thrombosis and restenosis, an expandable, intraluminal prosthesis, one example of which is a stent, is implanted in the lumen to maintain the vascular patency.

Stents act as scaffoldings, functioning to physically hold open and, if desired, to expand the wall of the passageway. Typically, stents are capable of being compressed so that they can be inserted through small lumens via catheters and then expanded to a larger diameter once they are at the desired location. Examples in the patent literature disclosing stents that have been applied in PTCA procedures include U.S. Pat. No. 4,733,665 issued to Palmaz, U.S. Pat. No. 4,800,882 issued to Gianturco, and U.S. Pat. No. 4,886,062 issued to Wiktor.

Mechanical intervention via stents has reduced the rate of restenosis as compared to balloon angioplasty. Yet, restenosis is still a significant clinical problem with rates ranging from 20–40%. When restenosis does occur in the stented segment, its treatment can be challenging, as clinical options are more limited as compared to lesions that were treated solely with a balloon.

Stents are used not only for mechanical intervention but also as vehicles for providing biological therapy. Biological therapy can be achieved by medicating the stents. Medicated stents provide for the local administration of a therapeutic substance at the diseased site. In order to provide an efficacious concentration to the treated site, systemic administration of such medication often produces adverse or even toxic side effects for the patient. Local delivery is a preferred method of treatment in that smaller total levels of medication are administered in comparison to systemic dosages, but are concentrated at a specific site. Local delivery thus produces fewer side effects and achieves more favorable results.

One proposed method for medicating stents included use of a heparin-coated metallic stent, whereby a heparin coating was ionically or covalently bonded to the stent. Significant disadvantages associated with the aforementioned method include loss of the therapeutic substance from the body of the stent during delivery and expansion of the stent as well as lack of control of the release rate of the substance from the stent.

Another proposed method of medicating stents involved the use of a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent strut surfaces a coating of the polymer and the therapeutic substance impregnated in the polymer.

Depending on the physiological mechanism targeted, the therapeutic substance may be required to be released at an efficacious concentration for an extended duration of time. Increasing the quantity of the therapeutic substance in the polymeric coating can lead to poor coating mechanical properties, inadequate coating adhesion, and overly rapid rate of release. Increasing the quantity of the polymeric compound by producing a thicker coating can perturb the geometrical and mechanical functionality of the stent as well as limit the procedures for which the stent can be used.

It is desirable to increase the residence time of a substance at the site of implantation, at a therapeutically useful concentration, without needing to add a greater percentage of the therapeutic substance to the polymeric coating and without needing to apply a significantly thicker coating.

SUMMARY OF THE INVENTION

In accordance with one embodiment of the present invention, a method of forming a coating for a medical device, such as a stent, carrying an agent is provided. The method includes applying a first composition including a polymer to at least a portion of a medical device to form a first polymeric coating. The polymer has a solubility parameter not greater than approximately 11.5 $(cal/cm^3)^{1/2}$. The first polymeric coating reduces the rate of release of the agent from the medical device. In some embodiments of the method, the polymer of the first coating additionally has an equilibrium water absorption factor of less than about 5% by weight under physiologic conditions.

Also provided is a composition for forming a coating on a medical device. The composition includes a solvent and a hydrophobic polymer dissolved in the solvent. The hydrophobic polymer has an equilibrium water absorption factor of less than about 5% by weight under physiological conditions. In some embodiments, the hydrophobic polymer additionally has a solubility parameter not greater than approximately 11.5 $(cal/cm^3)^{1/2}$.

An implantable medical device for carrying a therapeutic agent is also provided. The device includes a first coating including a polymeric material. The polymeric material has a solubility parameter not greater than approximately 11.5 $(cal/cm^3)^{1/2}$. The first coating reduces the rate of release of the agent. In some embodiments, the polymeric material additionally has an equilibrium water absorption factor of less than about 5% by weight under physiologic conditions.

Polymeric material suitable for use in the first coating of the present invention include hydrophobic and non-polar polymers such as, but not limited to, polytetrafluoroethylene, perfluoro elastomers, amorphous fluoropolymer, ethylene-tetrafluoroethylene copolymer, fluoroethylene-alkyl vinyl ether copolymer, polyhexafluoropropylene, low density linear polyethylenes having high molecular weights, ethylene-olefin copolymers, atactic polypropylene, polyisobutene, polybutylenes, styrene-ethylene-styrene block copolymers, styrene-butylene-styrene block copolymers, styrene-ethylene/butylene-styrene block copolymers, styrene-butadiene-styrene block copolymers, ethylene-anhydride copolymers, ethylene vinyl acetate copolymers, ethylene-acrylic acid copolymers, ethylene methacrylic acid copolymers, polyurethanes with a polydimethylsiloxane soft segment, and cross-linked silicone elastomers.

The medical device can be, for example, a balloon-expandable stent, a self-expandable stent, a graft, a stent graft. The medical device can include cavities containing an active ingredient for the release of the active ingredient when the device is implanted. Alternatively, the device can include a reservoir coating carrying an active ingredient.

DETAILED DESCRIPTION OF THE EMBODIMENTS

Figure 1A:
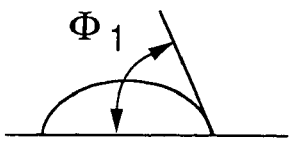
FIG. 1A illustrates a fluid on a solid substrate having a contact angle $\Phi_1$.

Composition for Forming an Optional Primer Layer

The presence of an active ingredient in a polymeric matrix can interfere with the ability of the matrix to adhere effectively to the surface of the device.

Increasing the quantity of the active ingredient reduces the effectiveness of the adhesion. High drug loadings of, for example, 10–40% by weight in the coating can hinder the retention of the coating on the surface of the device. A primer layer can serve as a functionally useful intermediary layer between the surface of the device and an active ingredient-containing or reservoir coating. The primer layer provides an adhesive tie between the reservoir coating and the device—which, in effect, would also allow for the quantity of the active ingredient in the reservoir coating to be increased without compromising the ability of the reservoir coating to be effectively contained on the device during delivery and, if applicable, expansion of the device.

The embodiments of the composition for an optional primer layer are prepared by conventional methods wherein all components are combined, then blended. More particularly, in accordance with one embodiment, a predetermined amount of a polymer or a prepolymer is added to a predetermined amount of a solvent or a combination of solvents. The mixture can be prepared at ambient pressure and under anhydrous atmosphere. Heating and stirring and/or mixing can be employed to effect dissolution of the polymer into the solvent.

"Polymer," "poly," and "polymeric" are defined as compounds that are the product of a polymerization reaction and are inclusive of homopolymers, copolymers, terpolymers etc., including random, alternating, block, and graft variations thereof. The polymers should have a high capacity of adherence to the surface of an implantable device, such as a metallic surface of a stent.

Representative examples of suitable polymeric materials include, but are not limited to, polyisocyanates, such as triisocyanurate and polyisocyanate polyether polyurethanes based on diphenylmethane diisocyanate; acrylates, such as copolymers of ethyl acrylate and methacrylic acid; titanates, such as tetra-iso-propyl titanate and tetra-n-butyl titanate; zirconates, such as n-propyl zirconate and n-butyl zirconate; silane coupling agents, such as 3-aminopropyltriethoxysilane and (3-glydidoxypropyl)methyldiethoxysilane; high amine content polymers, such as polyethyleneamine, polyallylamine, and polylysine; polymers with a high content of hydrogen bonding groups, such as polyethylene-co-polyvinyl alcohol, ethylene vinyl acetate, and melamine formaldehydes; and unsaturated polymers and prepolymers, such as polycaprolactone diacrylates, polyacrylates with at least two acrylate groups, and polyacrylated polyurethanes. With the use of unsaturated prepolymers, a free radical or UV initiator can be added to the composition for the thermal or UV curing or cross-linking process, as is understood by one of ordinary skill in the art.

Biocompatible polymers can also be used for the primer material. The polymer can be bioabsorbable or biostable. Bioabsorbable polymers that could be used include poly (hydroxyvalerate), poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), copoly(ether-esters) (e.g. PEO/PLA), polyalkylene oxalates, polyphosphazenes and biomolecules such as fibrin, fibrinogen, cellulose, starch, collagen and hyaluronic acid. In addition, biostable polymers such as polyurethanes, silicones, and polyesters could be used. Other polymers could also be used if they can be dissolved and cured or polymerized on the stent such as polyolefins, polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Ethylene vinyl alcohol is a very suitable choice of polymer for the primer layer. The copolymer possesses good adhesive qualities to the surface of a stent, particularly stainless steel surfaces, and has illustrated the ability to expand with a stent without any significant detachment of the copolymer from the surface of the stent. Ethylene vinyl alcohol copolymer, commonly known by the generic name EVOH or by the trade name EVAL, refers to copolymers comprising residues of both ethylene and vinyl alcohol monomers. One of ordinary skill in the art understands that ethylene vinyl alcohol copolymer may also be a terpolymer so as to include small amounts of additional monomers, for example less than about five (5) mole percentage of styrenes, propylene, or other suitable monomers. In a useful embodiment, the copolymer comprises a mole percent of ethylene of from about 27% to about 48%. Ethylene vinyl alcohol copolymers are available commercially from companies such as Aldrich Chemical Company, Milwaukee, Wis., or EVAL Company of America, Lisle, Ill., or can be prepared by conventional polymerization procedures that are well known to one of ordinary skill in the art.

The solvent should be compatible with the polymer and should be capable of placing the polymer into solution at the concentration desired. Particularly useful solvents should also be able to expand the chains of the polymer for maximum interaction with the surface of the device, such as a metallic surface of a stent. Examples of suitable solvents include, but are not limited to, dimethylsulfoxide (DMSO), chloroform, acetone, water (buffered saline), xylene, acetone, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, N-methyl pyrrolidinone, toluene and mixtures thereof.

By way of example, and not limitation, the polymer can comprise from about 0.1% to about 35%, more narrowly from about 2% to about 20% by weight of the total weight of the composition, and the solvent can comprise from about 65% to about 99.9%, more narrowly from about 80% to about 98% by weight of the total weight of the composition. A specific weight ratio is dependent on factors such as the material from which the implantable device is made, the geometrical structure of the device, the choice of polymer-solvent combination, and the method of application.

Figure 1B:
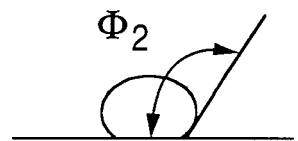
FIG. 1B illustrates a fluid on a solid substrate having a contact angle $\Phi_2$.

In accordance with another embodiment, a fluid can be added to the composition to enhance the wetting of the primer composition for a more uniform coating application. To enhance the wetting of the composition, a suitable fluid typically has a high capillary permeation. Capillary permeation or wetting is the movement of a fluid on a solid substrate driven by interfacial energetics. Capillary permeation is quantitated by a contact angle, defined as an angle at the tangent of a droplet in a fluid phase that has taken an equilibrium shape on a solid surface. A low contact angle indicates a higher wetting liquid. A suitably high capillary permeation corresponds to a contact angle less than about 90°. FIG. 1A illustrates a fluid droplet 10A on a solid substrate 12, for example a stainless steel surface. Fluid droplet 10A has a high capillary permeation that corresponds to a contact angle $\Phi_1$, which is less than about 90°. In contrast, FIG. 1B illustrates a fluid droplet 10B on solid substrate 12, having a low capillary permeation that corresponds to a contact angle $\Phi_2$, which is greater than about 90°. The wetting fluid, typically, should have a viscosity not greater than about 50 centipoise, narrowly about 0.3 to about 5 centipoise, more narrowly about 0.4 to about 2.5 centipoise. The wetting fluid, accordingly, when added to the composition, reduces the viscosity of composition.

The wetting fluid should be compatible with the polymer and the solvent and should not precipitate the polymer. The wetting fluid can also act as the solvent. Useful examples of the wetting fluid include, but are not limited to, tetrahydrofuran (THF), dimethylformamide (DMF), 1-butanol, n-butyl acetate, dimethyl acetamide (DMAC), and mixtures and combinations thereof. By way of example and not limitation, the polymer can comprise from about 0.1% to about 35%, more narrowly from about 2% to about 20% by weight of the total weight of the composition; the solvent can comprise from about 19.9% to about 98.9%, more narrowly from about 58% to about 84% by weight of the total weight of the composition; and the wetting fluid can comprise from about 1% to about 80%, more narrowly from about 5% to about 40% by weight of the total weight of the composition. The specific weight ratio of the wetting fluid depends on the type of polymer, solvent and wetting fluid employed as wells as the weight ratio of the polymer and the solvent.

Composition for Forming an Active Ingredient-Containing Coating

The embodiments of the composition for an active ingredient-containing or reservoir coating are prepared by conventional methods wherein all components are combined, then blended. More particularly, in accordance with one embodiment, a predetermined amount of a polymeric compound is added to a predetermined amount of a compatible solvent. The polymeric compound can be added to the solvent at ambient pressure and under anhydrous atmosphere. If necessary, gentle heating and stirring and/or mixing can be employed to effect dissolution of the polymer into the solvent, for example 12 hours in a water bath at about 60° C.

Sufficient amounts of an active ingredient are dispersed in the blended composition of the polymer and the solvent. The polymer can comprise from about 0.1% to about 35%, more narrowly from about 2% to about 20% by weight of the total weight of the composition, the solvent can comprise from about 59.9% to about 99.8%, more narrowly from about 79% to about 89% by weight of the total weight of the composition, and the active ingredient can comprise from about 0.1% to about 40%, more narrowly from about 1% to about 9% by weight of the total weight of the composition. More than 9% by weight of the active ingredient could adversely affect characteristics that are desirable in the polymeric coating, such as adhesion of the coating to the device. With the use of the optional primer layer, weight ratios of more than 9% for the active ingredient are achievable without compromising the effectiveness of the adhesion. Selection of a specific weight ratio of the polymer and solvent is dependent on factors such as, but not limited to, the material from which the device is made, the geometrical structure of the device, and the type and amount of the active ingredient employed.

Optionally, a second solvent, such as tetrahydrofuran (THF) or dimethylformamide (DMF), can be used to improve the solubility of an active ingredient in the composition. The second solvent can be added to the composition or the active ingredient can be added to the second solvent prior to admixture with the blend. In this embodiment, the polymer can comprise from about 0.1% to about 35%, more narrowly from about 2% to about 20% by weight of the total weight of the composition, the solvent can comprise from about 19.8% to about 98.8%, more narrowly from about 49% to about 79% by weight of the total weight of the composition; the second solvent can comprise from about 1% to about 80%, more narrowly from about 5% to about 40% by weight of the total weight of the composition;

and the active ingredient can comprise from about 0.1% to about 40%, more narrowly from about 1% to about 9% by weight of the total weight of the composition. Selection of a specific weight ratio of the polymer, the solvent, and the second solvent is dependent on factors such as, but not limited to, the material from which the implantable device is made, the geometrical structure of the device, and the type and amount of the active ingredient employed. The particular weight percentage of the active ingredient mixed within the composition depends on factors such as duration of the release, cumulative amount of release, and release rate that is desired.

The active ingredient should be in true solution or saturated in the blended composition. If the active ingredient is not completely soluble in the composition, operations including mixing, stirring, and/or agitation can be employed to effect homogeneity of the residues. The active ingredient can also be first added to the second solvent prior to admixing with the composition. The active ingredient may be added so that the dispersion is in fine particles. The mixing of the active ingredient can be conducted in an anhydrous atmosphere, at ambient pressure, and at room temperature such that supersaturating the active ingredient is not achieved.

The active ingredient may be any substance capable of exerting a therapeutic or prophylactic effect in the practice of the present invention. Examples of such active ingredients include antiproliferative, antineoplastic, antiinflammatory, antiplatelet, anticoagulant, antifibrin, antithrombin, antimitotic, antibiotic, and antioxidant substances as well as combinations thereof. A suitable example of an antiproliferative substance is actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. Examples of suitable antineoplastics include paclitaxel and docetaxel. Examples of suitable antiplatelets, anticoagulants, antifibrins, and antithrombins include sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIB/IIIa platelet membrane receptor antagonist, recombinant hirudin, thrombin inhibitor (available from Biogen), and 7E-3B® (an antiplatelet drug from Centocore). Examples of suitable antimitotic agents include methotrexate, azathioprine, vincristine, vinblastine, fluorouracil, adriamycin, and mutamycin. Examples of suitable cytostatic or antiproliferative agents include angiopeptin (a somatostatin analog from Ibsen), angiotensin converting enzyme inhibitors such as CAPTOPRIL (available from Squibb), CILAZAPRIL (available from Hoffman-LaRoche), or LISINOPRIL (available from Merck); calcium channel blockers (such as Nifedipine), colchicine, fibroblast growth factor (FGF) antagonists, histamine antagonist, LOVASTATIN (an inhibitor of HMG-CoA reductase, a cholesterol lowering drug from Merck), monoclonal antibodies (such as PDGF receptors), nitroprusside, phosphodiesterase inhibitors, prostaglandin inhibitor (available form Glazo), Seramin (a PDGF antagonist), serotonin blockers, thioprotease inhibitors, triazolopyrimidine (a PDGF antagonist), and nitric oxide. Other therapeutic substances or agents that may be appropriate include alpha-interferon; genetically engineered epithelial cells; dexamethasone; rapamycin; estradiol; clobetasol propionate; cisplatin; and carboplatin. Exposure of the composition to the active ingredient should not adversely alter the active ingredient's composition or characteristic. Accordingly, the particular active ingredient is selected for compatibility with the blended composition.

The dosage or concentration of the active ingredient required to produce a therapeutic effect should be less than the level at which the active ingredient produces toxic effects and greater than the level at which non-therapeutic results are obtained. The dosage or concentration of the active ingredient required to inhibit the desired cellular activity of the vascular region, for example, can depend upon factors such as the particular circumstances of the patient; the nature of the trauma; the nature of the therapy desired; the time over which the ingredient administered resides at the vascular site; and if other bioactive substances are employed, the nature and type of the substance or combination of substances. Therapeutically effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

The polymer chosen should be biocompatible so as not to cause any adverse response. The solvent chosen should be capable of placing the polymer into solution at the concentration desired. Representative examples of biocompatible polymers as well as of suitable solvents include those provided above with reference to the primer composition. With the use of a low ethylene content, e.g., 29 mol %, ethylene vinyl alcohol, for example, a suitable solvent is iso-propylalcohol (IPA) admixed with water e.g., from about 40% to about 60% by weight IPA. If an optional primer layer is used, the choice of polymer for the reservoir coating can be the same as that selected for the primer so as to eliminate any interfacial incompatibilities.

Composition for Forming the Rate-Reducing Membrane

If it is desired to increase the rate at which an active ingredient diffuses through a membrane, the membrane should be made of a polymer in which the active ingredient readily dissolves. By contrast, if it is desired to decrease the rate at which an active ingredient diffuses through a membrane, the membrane should be made of a polymer in which the active ingredient is less soluble. The purpose of the rate-reducing membrane of the present invention is to decrease the rate of release of an underlying active ingredient. Accordingly, the polymer for forming the rate-reducing membrane should be selected such that the active ingredient may not readily dissolve therein.

Polar substances are substances that have a dipole moment $\mu$ greater than 0 Debye. As a general rule, polar substances dissolve well in other polar substances, such as water. Accordingly, polar substances can be broadly categorized as "hydrophilic." Polar substances typically dissolve less readily in non-polar substances, which can be broadly categorized as "hydrophobic." The syllogism follows that a polar active ingredient will not readily dissolve in a hydrophobic polymer. Accordingly, a polymeric membrane that is hydrophobic may be employed to reduce the rate at which a polar active ingredient is released from an implantable device, such as a stent.

One method of defining the hydrophobicity of a polymer is by the solubility parameter of the polymer. The solubility parameter is represented by Equation 1:

$$\delta = (\Delta E/V)^{1/2} \quad \text{(Equation 1)}$$

where
- $\delta$=solubility parameter ($(cal/cm^3)^{1/2}$)
- $\Delta E$=energy of vaporization (cal)
- $V$=molar volume ($cm^3$)

("Polymer Handbook", 2nd Ed., Brandrup J. and. E H Immergut, ed., Wiley-Interscience, John Wiley & Sons, N.Y. (1975)). Because polymers are typically non-volatile and thus cannot be vaporized without decomposition, the solubility parameter is measured indirectly. Briefly, solvents in which a polymer dissolves without a change in heat or volume are identified. The solubility parameter of the polymer is then defined to be the same as the solubility parameters of the identified solvents.

As a general rule, the value of the solubility parameter $\delta$ is inversely proportional to the degree of hydrophobicity of a polymer. Polymers that are very hydrophobic may have a low solubility parameter value. This general proposition is particularly applicable for polymers having a glass transition temperature below physiological temperature. A polymer that is sufficiently hydrophobic for use in the rate-limiting membrane of the present invention can have a solubility parameter not more than about 11.5 $(cal/cm^3)^{1/2}$, more narrowly not more than about 10 $(cal/cm^3)^{1/2}$, even more narrowly not more than 8.5 $(cal/cm^3)^{1/2}$.

Table 1 illustrates the solubility parameters of various polymers.

TABLE 1

| Polymer | Solubility Parameter $(cal/cm^3)^{1/2}$ |
|---|---|
| polytetrafluoroethylene | 6.2 |
| polydimethylsiloxane | 7.3–7.62 |
| polyethylene | 7.7–8.79 |
| polybutylmethacrylate | 8.3–8.8 |
| polypropylene | 9.2–9.4 |
| ethyl cellulose | 10.3 |
| polyvinyl acetate | 9.4–11.0 |

Another method of defining the hydrophobicity of a polymer is by the equilibrium moisture absorption factor. The equilibrium moisture absorption factor is represented by Equation 2:

$$MAF = (W_w/W_p + W_w) \times 100 \quad \text{(Equation 2)}$$

where
- MAF=equilibrium moisture absorption factor (%)
- $W_w$=weight of water taken up by the polymer when immersed in water or exposed to physiologic conditions
- $W_p$=weight of the polymer Generally, the less water absorbed by a polymer, and thus the lower the equilibrium moisture absorption factor, the better the polymer functions as a diffusion barrier for a polar active ingredient. Upon absorption of water, a polymer can swell and the spaces between polymer chains can enlarge, allowing an active ingredient to diffuse more easily through the polymer. In addition, absorbed water provides an otherwise non-polar polymer with polar water groups. These polar regions more readily dissolve a polar active ingredient via hydrogen bonding interactions, thereby allowing the active ingredient to diffuse through the otherwise non-polar polymer more quickly. Thus, a polymer that is sufficiently hydrophobic for use in the rate-limiting membrane of the present invention should have an equilibrium moisture absorption factor of less than about 5% by weight, more narrowly less than about 2%. Representative examples of such polymers include polytetrafluoroethylene, perfluoro elastomers, fluoropolymers such as polyvinylidene fluoride, ethylene-tetrafluoroethylene copolymer, fluoroethylene-alkyl vinyl ether copolymer, polyhexafluoropropylene, low density linear polyethylenes having high molecular weights, ethylene-olefin copolymers, atactic polypropylene, polyisobutene, polybutylenes, polybutenes, styrene-ethylene-styrene block copolymers, styrene-butylene-styrene block copolymers, styrene-ethylene/butylene-styrene block copolymers, styrene-butadiene-styrene block copolymers, ethylene-anhydride copolymers, ethylene vinyl acetate copolymers, polybutylmethacrylate, ethylene-acrylic acid copolymers of low acrylic acid content, ethylene methacrylic acid copolymers of low methacrylic acid content, ethylene vinyl alcohol copolymers with an ethylene content greater than 48 mole percent, and cross-linked silicone elastomers.

In addition to having a solubility parameter not more than about 11.5 $(cal/cm^3)^{1/2}$ and/or an equilibrium moisture absorption factor of less than about 5% by weight, the selected polymer should be biocompatible. The polymer should also be capable of being placed into solution at a desired concentration by a selected solvent, such as a non-polar solvent so as to prevent dissolution of the polar active ingredient with the non-polar solvent. Prevention of dissolution of the active ingredient during the coating process of the rate-limiting layer significantly reduces or eliminates the migration or leaching of the active component out from the underlying reservoir layer or device. Accordingly, the quantity of active ingredient will not be reduced during the application of the rate-limiting layer.

Fluoropolymers are a suitable choice for the barrier layer composition. For example, the solubility parameter of polytetrafluoroethylene is about 6.2 $(cal/cm^3)^{1/2}$, and the equilibrium moisture absorption factor is about 0.01%. Solution processing of fluoropolymers is possible, particularly the low crystallinity varieties such as CYTOP available from Asahi Glass and TEFLON AF available from DuPont. Solutions of up to about 15% (wt/wt) are possible in perfluoro solvents, such as FC-75 (available from 3M under the brand name FLUORINERT), which are non-polar, low boiling solvents. Such volatility allows the solvent to be easily and quickly evaporated following the application of the polymer-solvent solution to the medical device.

Another particularly suitable choice of polymer for the barrier layer composition is styrene-ethylene/butylene-styrene block copolymer. The solubility parameter of this material lies in the range of from about 7.7 $(cal/cm^3)^{1/2}$ to about 10.3 $(cal/cm^3)^{1/2}$, and the equilibrium moisture absorption factor is less than about 1%. Styrene-ethylene/butylene-styrene block copolymer, e.g., Kraton G-series, can be dissolved in non-polar solvents such as, but not limited to, toluene, xylene, and decalin.

Still other suitable choices of polymers for the rate-limiting membrane include, but are not limited to, ethylene-anhydride copolymers; ethylene vinyl acetate copolymers having, for example, a mol % of vinyl acetate of from about 9% to about 25%; and ethylene-acrylic acid copolymers having, for example, a mol % of acrylic acid of from about 2% to about 25%. The ethylene-anhydride copolymer available from Bynel adheres well to EVAL and thus would function well as a topcoat over a reservoir layer made from EVAL. The copolymer can be dissolved in organic solvents, such as dimethylsulfoxide and dimethylacetamide. Ethylene vinyl acetate polymers can be dissolved in organic solvents, such as toluene and n-butyl acetate. Ethylene-acrylic acid copolymers can be dissolved in organic solvents, such as methanol, isopropyl alcohol, and dimethylsulfoxide.

Yet another suitable choice of polymer for the rate-limiting membrane composition is a cross-linked silicone elastomer. Such substances have a solubility parameter in the range of about 7.3 $(cal/cm^3)^{1/2}$ to about 7.6 $(cal/cm^3)^{1/2}$, and an equilibrium moisture absorption factor of less than about 0.5%. Loose silicone and silicone with very low cross-linking are thought to cause an inflammatory biological response. However, it is believed that a thoroughly cross-linked silicone elastomer, having low levels of leachable silicone polymer and oligomer, is an essentially non-inflammatory substance. Silicone elastomers, such as Nusil MED-4750, MED-4755, or MED2–6640, having high tensile strengths, for example between 1200 psi and 1500 psi, will likely have the best durability during crimping, delivery, and expansion of a stent as well as good adhesion to a reservoir layer, e.g., EVAL or the surface of a medical device.

The embodiments of the composition for a rate-reducing membrane or diffusion barrier layer are prepared by methods wherein all components are combined, then blended. More particularly, in accordance with one embodiment, a predetermined amount of a polymeric compound is added to a predetermined amount of a compatible solvent. The selected solvent should be capable of placing the polymer into solution at the concentration desired.

The polymeric compound can be added to the solvent at ambient pressure and under anhydrous atmosphere. If necessary, gentle heating and stirring and/or mixing can be employed to effect dissolution of the polymer into the solvent, for example 12 hours in a water bath at about 60° C. The polymer can comprise from about 0.1% to about 35%, more narrowly from about 2% to about 20% by weight of the total weight of the composition, and the solvent can comprise from about 65% to about 99.9%, more narrowly from about 80% to about 98% by weight of the total weight of the composition. Selection of a specific weight ratio of the polymer and solvent is dependent on factors such as, but not limited to, the type of polymer and solvent employed, the type of underlying reservoir layer, and the method of application. Optionally, one of the aforementioned wetting fluids can also be added to the blend.

EXAMPLES OF THE DEVICE

The device or prosthesis used in conjunction with the above-described compositions may be any suitable medical substrate that can be implanted in a human or veterinary patient. Examples of such implantable devices include self-expandable stents, balloon-expandable stents, stent-grafts, grafts, artificial heart valves, cerebrospinal fluid shunts, and pacemaker electrodes. The underlying structure of the device can be virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

It should be noted that the rate-reducing membrane or diffusion barrier layer in accordance with various embodiments of the present invention can be used without the active ingredient-containing coating. In such embodiments, the device may include cavities or micro-pores for containing the active ingredient such that the diffusion barrier layer is disposed over the cavities. The device can be formed by sintering the stent material from metallic particles, filaments, fibers or other materials. The device can be formed from a sintered wire that is coiled or otherwise formed into a device. The prosthesis can also be formed from a sintered cylindrical tube or sintered metal sheet which can be laser cut or chemical etched into an expandable stent structure. Formation of cavities via a sintering process is described in U.S. Pat. No. 5,843,172 to Yan. By way of another example, the surface of the device can be exposed to an etchant or a laser discharge to form cavities of selected dimensional specification.

Methods For Applying the Compositions to the Device

To form the optional primer layer and/or the active ingredient-containing coating on a surface of the device or prosthesis, the surface of the device should be clean and free from contaminants that may be introduced during manufacturing. However, the surface of the prosthesis requires no particular surface treatment to retain the applied coating. Application of the composition can be by any conventional method, such as by spraying the composition onto the prosthesis or by immersing the prosthesis in the composition. Operations such as wiping, centrifugation, blowing, or other web-clearing acts can also be performed to achieve a more uniform coating. Briefly, wiping refers to physical removal of excess coating from the surface of the stent; centrifugation refers to rapid rotation of the stent about an axis of rotation; and blowing refers to application of air at a selected pressure to the deposited coating. Any excess coating can also be vacuumed off the surface of the device. The addition of a wetting fluid leads to a consistent application of the composition which also causes the coating to be uniformly deposited on the surface of the prosthesis.

With the use of the thermoplastic polymers for the primer, such as ethylene vinyl alcohol copolymer, polycaprolactone, poly(lactide-co-glycolide), poly(hydroxybutyrate), etc., the deposited primer composition should be exposed to a heat treatment at a temperature range greater than about the glass transition temperature ($T_g$) and less than about the melting temperature ($T_m$) of the selected polymer. Unexpected results have been discovered with treatment of the composition under this temperature range, specifically strong adhesion or bonding of the coating to the metallic surface of a stent. The device should be exposed to the heat treatment for any suitable duration of time that would allow for the formation of the primer coating on the surface of the device as well as for the evaporation of the solvent or combination of solvent and wetting fluid. It is understood that essentially all of the solvent and the wetting fluid will be removed from the composition, but traces or residues may remain blended with the polymer.

Table 2 lists the $T_g$ and $T_m$ for some of the polymers used in the embodiments of the present invention. $T_g$ and $T_m$ of polymers are attainable by one of ordinary skill in the art.

The cited exemplary temperature and time for exposure are provided by way of illustration and are not meant to be limiting.

TABLE 2

| Polymer | $T_g$ (° C.) | $T_m$ (° C.) | Exemplary Temperature (° C.) | Exemplary Duration of Time For Heating |
|---|---|---|---|---|
| EVAL | 55 | 165 | 140 | 4 hours |
| polycaprolactone | −60 | 60 | 50 | 2 hours |
| ethylene vinyl acetate (e.g., 33% vinyl acetate content) | 36 | 63 | 45 | 2 hours |
| Polyvinyl alcohol | 75–85* | 200–220* | 165 | 2 hours |

*Exact temperature depends on the degree of hydrolysis which is also known as the amount of residual acetate.

With the use of one of the aforementioned thermoset primer polymers, the use of initiators may be required. By way of example, epoxy systems consisting of diglycidyl ether of bisphenol A resins can be cured with amine curatives, thermoset polyurethane prepolymers can cured with polyols, polyamines, or water (moisture), and acrylated urethane can be cured with UV light. If baked, the temperature can be above the $T_g$ of the selected polymer.

With the use of the inorganic primer polymers, such as silanes, titanates, and zirconates, the solvent is allowed to evaporate.

The composition containing the active ingredient can be applied to a designated region of the primer coating or the surface of the device. The solvent(s) or the combination of solvent(s) and the wetting fluid is removed from the composition by allowing the solvent(s) or combination of the solvent(s) and the wetting fluid to evaporate. The evaporation can be induced by heating the device at a predetermined temperature for a predetermined period of time. For example, the device can be heated at a temperature of about 60° C. for about 12 hours to about 24 hours. The heating can be conducted in an anhydrous atmosphere and at ambient pressure and should not exceed the temperature which would adversely affect the active ingredient. The heating can, alternatively, be conducted under a vacuum condition. It is understood that essentially all of the solvent and the wetting fluid will be removed from the composition, but traces or residues may remain blended with the polymer.

The diffusion barrier layer can be formed on a designated region of the active ingredient-containing coating subsequent to the evaporation of the solvent(s) or solvent(s)/wetting fluid and the drying of the polymer for the active ingredient-containing coating. Alternatively, in embodiments in which a polymeric reservoir coating is not employed, the rate-reducing membrane may be formed directly over active-ingredient containing cavities within the surface of the prosthesis. The diffusion barrier layer can be applied by spraying the composition onto the device or immersing the device in the composition, then drying the polymer. The above-described processes can be similarly repeated for the formation of the diffusion barrier layer.

Coating

Figure 2A:
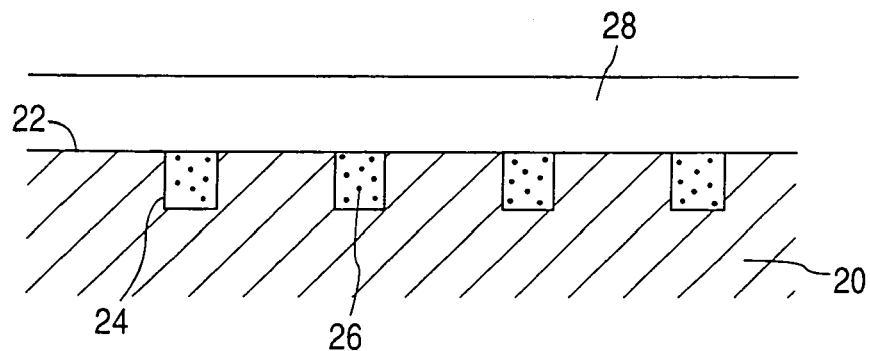
FIG. 2A illustrates a first coating deposited over an implantable medical substrate in accordance with one embodiment of the present invention.
Figure 2B:
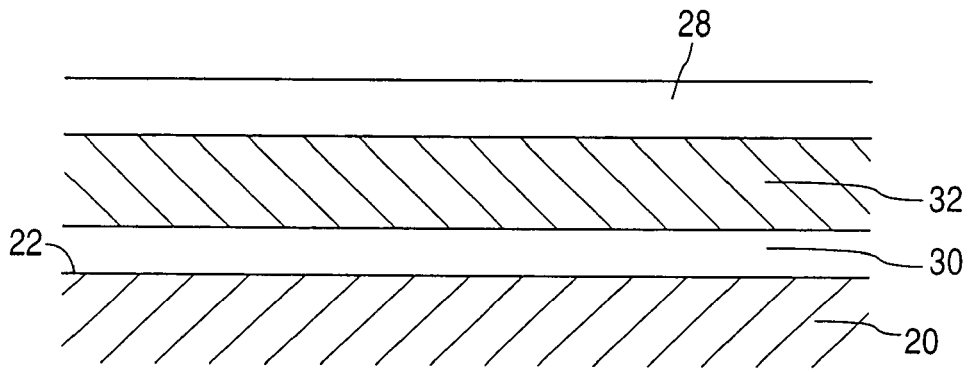
FIG. 2B illustrates a first coating deposited over an implantable medical substrate in accordance with another embodiment of the present invention.
Figure 2C:
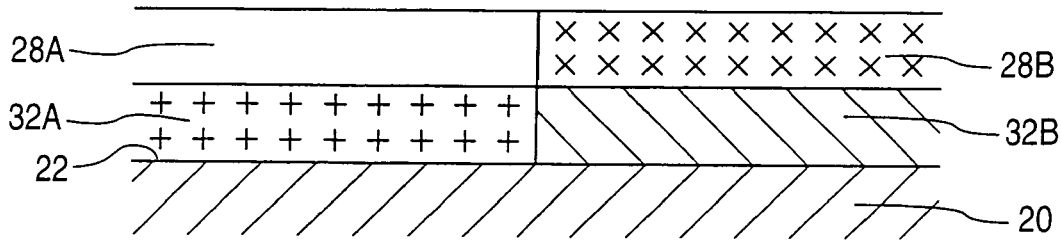
FIG. 2C illustrates a pair of coatings deposited over an implantable medical substrate in accordance with yet another embodiment of the present invention.

Some of the various embodiments of the present invention are illustrated by FIGS. 2A, 2B, and 2C. The Figures have not been drawn to scale, and the thickness of the various layers have been over or under emphasized for illustrative purposes.

Referring to FIG. 2A, a body of a medical substrate 20, such as a stent, is illustrated having a surface 22. Medical substrate 20 includes cavities or micro-pores 24 formed in the body for releasably containing an active ingredient, as illustrated by dotted region 26. A diffusion barrier layer or rate-reducing membrane 28 is disposed on surface 22 of medical substrate 20, covering cavities 24. Diffusion barrier layer 28 functions to reduce the rate of release of an active ingredient from medical substrate 20.

Referring to FIG. 2B, medical substrate 20 is illustrated having a primer layer 30 formed on surface 22. An active ingredient-containing or reservoir coating 32 is deposited on primer layer 30. Primer layer 30 serves as an intermediary layer for increasing the adhesion between reservoir coating 32 and surface 22. Increasing the amount of active ingredient admixed within the polymer diminishes the adhesiveness of reservoir layer 32 to surface 22. Accordingly, using an active ingredient-free polymer as an intermediary primer layer 30 allows for a higher active ingredient content for reservoir layer 32. Diffusion barrier 28 is formed over at least a selected portion of reservoir layer 32. One of ordinary skill in the art can appreciate that diffusion barrier layer 28 can be deposited only on selected areas of reservoir layer 32 so as to provide a variety of selected release parameters. Such selected patterns may become particularly useful if a combination of active ingredients are used, each of which requires a different release parameter.

FIG. 2C illustrates medical substrate 20 having a first reservoir layer 32A disposed on a selected portion of surface 22 of medical substrate 20. First reservoir layer 32A contains a first active ingredient, e.g., actinomycin D. A second reservoir layer 32B can also be disposed on surface 22. Second reservoir layer 32B contains a second active ingredient, e.g., taxol. First and second reservoir layers 32A and 32B are covered by first and second diffusion barrier layers 28A and 28B, respectively. In accordance with one embodiment, the polymeric material from which diffusion barrier layer 28A is made can be different than the material from which diffusion barrier layer 28B is made. Accordingly, a wide array of release parameters can be obtained for any selected combination of active ingredients.

Diffusion barrier layer 28 can have any suitable thickness, as the thickness of diffusion barrier layer 28 is dependent on parameters such as, but not limited to, the desired rate of release and the procedure for which the stent will be used.

Diffusion barrier layer 28 can have a thickness of about 0.1 to about 10 microns, more narrowly from about 0.25 to about 5 microns.

By way of example, and not limitation, the impregnated reservoir layer 32 can have a thickness of about 0.5 microns to about 1.5 microns. The particular thickness of reservoir layer 32 is based on the type of procedure for which medical substrate 20 is employed and the amount of the active ingredient to be delivered.

The amount of the active ingredient to be included on the prosthesis can be further increased by applying a plurality of reservoir layers 32 on top of one another. The optional primer layer 30 can have any suitable thickness, examples of which can be in the range of about 0.1 to about 10 microns, more narrowly about 0.1 to about 2 microns.

Method of Use

In accordance with the above-described method, the active ingredient can be applied to a device, e.g., a stent, retained on the device during delivery and released at a desired control rate and for a predetermined duration of time at the site of implantation. A stent having the above-described coating layers is useful for a variety of medical procedures, including, by way of example, treatment of obstructions caused by tumors in bile ducts, esophagus, trachea/bronchi and other biological passageways. A stent having the above-described coating layers is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

Briefly, an angiogram is first performed to determine the appropriate positioning for stent therapy. Angiography is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter, which allows a stent in its collapsed configuration to be inserted into the passageway. The delivery catheter is inserted either percutaneously, or by surgery, into the femoral artery, brachial artery, femoral vein, or brachial vein, and advanced into the appropriate blood vessel by steering the catheter through the vascular system under fluoroscopic guidance. A stent having the above-described coating layers may then be expanded at the desired area of treatment. A post insertion angiogram may also be utilized to confirm appropriate positioning.

EXAMPLES

The embodiments of the invention will be illustrated by the following set forth prophetic examples which are being given by way of illustration only and not by way of limitation. All parameters and data are not to be construed to unduly limit the scope of the embodiments of the invention.

Example 1

A 13 mm, 316L stainless steel TETRA stent is primer coated by spraying with a 2% (w/w) solution of poly (ethylene-co-vinyl alcohol) (44 mole % ethylene) in dimethylacetamide. The solvent is removed by baking at 140° C. for 1 hour. A solution of 2% (w/w) EVAL and 0.25% (w/w) actinomycin D in dimethylacetamide is spray coated onto the stent to a thickness that gives 25 µg of actinomycin D on the stent. The stent is then baked at 50° C. for two hours. A hydrophobic release rate limiting membrane is formed by spraying the stent with a 2% (w/w) solution of polybutylmethacrylate in a 1/3 (w/w) mixture of ethyl acetate and cyclohexanone. A second two hour bake at 50° C. is performed to remove the solvent.

Example 2

A 13 mm, 316L stainless steel TETRA stent is primer coated by spraying with a 2% (w/w) solution of poly (ethylene-co-vinyl alcohol) (44 mole % ethylene) in dimethylacetamide. The solvent is removed by baking at 140° C. for 1 hour. A solution of 2% (w/w) EVAL and 0.5% (w/w) paclitaxel in dimethylacetamide is spray coated onto the stent to a thickness that gives 50 µg of paclitaxel on the stent. The stent is then baked at 50° C. for two hours. A hydrophobic release rate limiting membrane is formed by spraying on a 2% (w/w) solution of poly(ethylene-co-vinylacetate) (25 mole % acetate content) in a 1/1 (w/w) solution of toluene and n-butyl acetate. Another two hour bake at 50° C. is performed to remove the solvent.

Example 3

A 13 mm, 316L stainless steel TETRA stent is primer coated by spraying with a 2% (w/w) solution of poly (ethylene-co-vinyl alcohol) (44 mole % ethylene) in dimethylacetamide. The solvent is removed by baking at 140° C. for 1 hour. A solution of 2% (w/w) EVAL and 0.67% (w/w) clobetasol propionate in dimethylacetamide is spray coated onto the stent to a thickness that gives 150 µg of clobetasol propionate on the stent. The stent is then baked at 50° C. for two hours. A hydrophobic release rate limiting membrane is formed by coating on a 5% (w/w) solution of Nusil MED3-6605 silicone dispersion in a 1/1 (w/w) of trichloroethylene and cyclohexane. This process is accomplished by placing the stent on a section of 0.070 inch OD stainless steel tubing. The coating is then applied to the stent via syringe. With the stent covered with fluid, it is pushed along the length of the tube with a short section of TEFLON tubing, while simultaneously rotating the stainless steel tube. The coating is left to air cure at ambient temperature for 18 hours.

While particular embodiments of the present invention have been shown and described, it will be obvious to those skilled in the art that changes and modifications can be made without departing from this invention in its broader aspects. For example, while much of the above discussion focuses on the reduction of the rate of diffusion of a polar active ingredient, one of ordinary skill in the art will understand that the diffusion barriers described are also applicable for use with non-polar active ingredients. Therefore, the appended claims are to encompass within their scope all such changes and modifications as fall within the true spirit and scope of this invention.

What is claimed is:

1. A stent having a therapeutic agent, comprising:
   (a) a first coating or layer over a surface of a stent;
   (b) a second coating or layer comprising a polymer and an agent over the first coating or layer; and
   (c) a third coating or layer comprising a polymer over the second coating or layer, the polymer having a solubility parameter not greater than approximately 11.5 $(cal/cm^3)^{1/2}$,
   wherein the third coating or layer reduces the rate of release of the agent.

2. The stent of claim 1, wherein the agent comprises rapamycin.

3. The stent of claim 1, wherein the agent comprises docetaxel or paclitaxel.

4. The stent of claim 1, wherein the solubility parameter is not greater than approximately 10 $(cal/cm^3)^{1/2}$.

5. The stent of claim 4, wherein the agent comprises rapamycin.

6. The stent of claim 4, wherein the agent comprises docetaxel or paclitaxel.

7. The stent of claim 1, wherein the solubility parameter is not greater than approximately 8.5 $(cal/cm^3)^{1/2}$.

8. The stent of claim 7, wherein the agent comprises rapamycin.

9. The stent of claim 7, wherein the agent comprises docetaxel or paclitaxel.

10. The stent of claim 1, wherein the polymer of the third coating or layer has an equilibrium water absorption factor of less than about 5% by weight under physiologic conditions.

11. The stent of claim 10, wherein the agent comprises rapamycin.

12. The stent of claim 10, wherein the agent comprises docetaxel or paclitaxel.

13. A stent having a therapeutic agent, comprising:
(a) a first coating or layer comprising a polymer and an agent for a stent; and
(b) a second coating or layer comprising a polymer over the first coating or layer, the polymer having a solubility parameter not greater than approximately 11.5 $(cal/cm^3)^{1/2}$, wherein the second coating or layer reduces the rate of release of the agent.

14. The stent of claim 13, wherein the agent comprises rapamycin.

15. The stent of claim 13, wherein the agent comprises docetaxel or paclitaxel.

16. The stent of claim 13, wherein the solubility parameter is not greater than approximately 10 $(cal/cm^3)^{1/2}$.

17. The stent of claim 16, wherein the agent comprises rapamycin.

18. The stent of claim 16, wherein the agent comprises docetaxel or paclitaxel.

19. The stent of claim 13, wherein the solubility parameter is not greater than approximately 8.5 $(cal/cm^3)^{1/2}$.

20. The stent of claim 19, wherein the agent comprises rapamycin.

21. The stent of claim 19, wherein the agent comprises docetaxel or paclitaxel.

22. The stent of claim 13, wherein the polymer of the second coating or layer has an equilibrium water absorption factor of less than about 5% by weight under physiologic conditions.

23. The stent of claim 22, wherein the agent comprises rapamycin.

24. The stent of claim 22, wherein the agent comprises docetaxel or paclitaxel.

25. The stent of claim 13, wherein the stent is a balloon expandable or self-expandable metallic stent.

26. The stent of claim 13, additionally comprising a primer beneath the first coating or layer.

27. A stent having a therapeutic agent, comprising:
(a) a first coating comprising a polymer and an agent for the stent; and
(b) a second coating comprising a polymer over the first coating, the second coating having a solubility parameter not greater than a parameter selected from the group consisting of about 11.5 $(cal/cm^3)^{1/2}$, about 10 $(cal/cm^3)^{1/2}$, and about 8.5 $(cal/cm^3)^{1/2}$.

28. The stent of claim 27, wherein the agent is rapamycin.

29. The stent of claim 27, wherein the agent is docetaxel or paclitaxel.

30. The stent of claim 27, wherein the second coating has an equilibrium water absorption factor of less than about 5% by weight under physiologic conditions.

31. The stent of claim 30, wherein the agent is rapamycin.

32. The stent of claim 30, wherein the agent is docetaxel or paclitaxel.

33. A stent comprising a coating having a first region including rapamycin and a second region above the first region, the second region including a polymer having a solubility parameter not greater than approximately 11.5 $(cal/cm^3)^{1/2}$.

34. The stent of claim 33, wherein the polymer has an equilibrium water absorption factor of less than about 5% by weight under physiologic conditions.

35. The stent of claim 33, wherein the solubility parameter is not greater than approximately 10 $(cal/cm^3)^{1/2}$.

36. The stent of claim 33, wherein the solubility parameter is not greater than approximately 8.5 $(cal/cm^3)^{1/2}$.

37. A stent comprising a coating having a first region including docetaxel or paclitaxel and a second region above the first region, the second region including a polymer having a solubility parameter not greater than approximately 11.5 $(cal/cm^3)^{1/2}$.

38. The stent of claim 37, wherein the polymer has an equilibrium water absorption factor of less than about 5% by weight under physiologic conditions.

39. The stent of claim 37, wherein the solubility parameter is not greater than approximately 10 $(cal/cm^3)^{1/2}$.

40. The stent of claim 37, wherein the solubility parameter is not greater than approximately 8.5 $(cal/cm^3)^{1/2}$.

41. A stent comprising a radially expandable metallic body and a coating on the body, the coating having a first region including rapamycin and a second region above the first region, the second region having a solubility parameter not greater than approximately 11.5 $(cal/cm^3)^{1/2}$.

42. The stent of claim 41, wherein the solubility parameter is not greater than approximately 10 $(cal/cm^3)^{1/2}$.

43. The stent of claim 41, wherein the solubility parameter is not greater than approximately 8.5 $(cal/cm^3)^{1/2}$.

44. The stent of claim 41, wherein the second region has an equilibrium water absorption factor of less than about 5% by weight under physiologic conditions.

45. A stent comprising a radially expandable metallic body and a coating on the body, the coating having a first region including docetaxel or paclitaxel and a second region above the first region, the second region having a solubility parameter not greater than approximately 11.5 $(cal/cm^3)^{1/2}$.

46. The stent of claim 45, wherein the solubility parameter is not greater than approximately 10 $(cal/cm^3)^{1/2}$.

47. The stent of claim 45, wherein the solubility parameter is not greater than approximately 8.5 $(cal/cm^3)^{1/2}$.

48. The stent of claim 45, wherein the second region has an equilibrium water absorption factor of less than about 5% by weight under physiologic conditions.

49. A method of forming a coating for a stent, comprising:
(a) forming a first coating or layer including an agent on the stent;
(b) forming a second coating or layer including a polymer over the first coating or layer, the polymer of the second coating or layer having a solubility parameter not greater than approximately 11.5 $(cal/cm^3)^{1/2}$, wherein the second coating reduces the rate of release of the agent.

50. The method of claim 49, additionally including forming a primer on the surface of the stent, beneath the first coating or layer.

51. The method of claim 49, wherein the agent comprises rapamycin.

52. The method of claim 49, wherein the agent comprises docetaxel or paclitaxel.

53. The method of claim 49, wherein the solubility parameter is not greater than approximately 10 $(cal/cm^3)^{1/2}$.

54. The method of claim 53, wherein the agent comprises rapamycin.

55. The method of claim 53, wherein the agent comprises docetaxel or paclitaxel.

56. The method of claim 49, wherein the solubility parameter is not greater than approximately 8.5 $(\text{cal/cm}^3)^{1/2}$.

57. The method of claim 56, wherein the agent comprises rapamycin.

58. The method of claim 56, wherein the agent comprises docetaxel or paclitaxel.

59. The method of claim 49, wherein the polymer of the second coating has an equilibrium water absorption factor of less than about 5% by weight under physiologic conditions.

60. The method of claim 59, wherein the agent comprises rapamycin.

61. The method of claim 59, wherein the agent comprises docetaxel or paclitaxel.

62. The method of claim 49, wherein the forming the second coating or layer comprises applying a composition including the polymer and a non-polar solvent on the first coating or layer.

63. The method of claim 62, wherein the agent is polar.

64. The method of claim 49, wherein the forming the second coating or layer comprises applying a composition including the polymer and a solvent over the first coating or layer, wherein the agent doesn't dissolve in the solvent.

65. The method of claim 49, wherein the forming the second coating or layer comprises applying a composition including the polymer and a solvent over the first coating or layer, wherein the composition does not cause a leaching out of the agent out from the first coating or layer.

* * * * *